United States Patent [19]

Bateman et al.

[11] Patent Number: 4,546,197

[45] Date of Patent: Oct. 8, 1985

[54] PHARMACEUTICAL COMPOSITION AND PROCESS FOR THE MANUFACTURE THEREOF

[75] Inventors: Neil E. Bateman, Melbourne; Ross A. Woods, Brunswick, both of Australia

[73] Assignee: R. P. Scherer Corporation, Troy, Mich.

[21] Appl. No.: 478,488

[22] Filed: Mar. 24, 1983

[30] Foreign Application Priority Data

Mar. 24, 1982 [AU] Australia .................. PF3284

[51] Int. Cl.⁴ .............................................. C07C 69/90
[52] U.S. Cl. ............................................................ 560/66
[58] Field of Search ........................................... 560/66

[56] References Cited

U.S. PATENT DOCUMENTS

| | | | |
|---|---|---|---|
| 2,070,240 | 2/1937 | Ruben | 560/66 |
| 2,151,185 | 3/1939 | Carruthers et al. | 260/484 |
| 2,282,557 | 5/1942 | Bruson | 260/410.5 |
| 2,331,169 | 10/1943 | Bruson | 260/410.5 |
| 3,012,064 | 12/1961 | Hertling et al. | 260/474 |
| 3,119,739 | 1/1964 | Campbell | 424/230 |
| 3,279,990 | 10/1966 | Rose et al. | 167/65 |
| 3,420,830 | 1/1969 | Fried | 260/244 |
| 3,461,152 | 8/1969 | Pouget | 560/66 |
| 3,644,424 | 2/1972 | Sherlock | 260/340.9 |
| 3,652,609 | 3/1972 | Alburn et al. | 260/408 |
| 3,652,665 | 3/1972 | Shen et al. | 560/66 |
| 3,673,212 | 6/1972 | Denss et al. | 260/326.3 |
| 3,741,985 | 6/1973 | Fried | 260/340.2 |
| 3,767,801 | 10/1973 | Tuma et al. | 424/230 |
| 3,988,446 | 10/1976 | Paris et al. | 424/230 |
| 4,046,887 | 9/1977 | Paris et al. | 424/232 |
| 4,136,165 | 1/1979 | Möller | 424/60 |
| 4,137,317 | 6/1979 | Paris et al. | 424/256 |

FOREIGN PATENT DOCUMENTS

| | | | |
|---|---|---|---|
| 0070049 | 1/1983 | European Pat. Off. | 560/66 |
| 1035175 | 7/1966 | United Kingdom | 560/66 |
| 1539149 | 1/1979 | United Kingdom | 560/66 |

OTHER PUBLICATIONS

*Chemical Abstracts*, vol. 97, 033133b (1982).
*Chemical Abstracts*, vol. 96, 20537r (1982).
*Chemical Abstracts*, vol. 96, 15063d (1982).
L. B. Witkin et al., *J. Pharmacol. Exptl. Therap.*, vol. 133, p. 400 (1961).
C. A. Winter et al., *Proc. Soc. Exp. Biol. Med.*, vol. 111, p. 544 (1962).
J. March, *Advanced Organic Chemistry: Reactions, Mechanisms and Structure*, McGraw-Hill, New York (1968), pp. 319–324.
C. Rüchardt et al., Liebigs Ann. Chem., 15–23 (1974).
Paris, G. Y. et al., J. Med. Chem. 1980, 23, 79–82.

*Primary Examiner*—Paul J. Killos
*Attorney, Agent, or Firm*—Allegretti, Newitt, Witcoff & McAndrews, Ltd.

[57] ABSTRACT

An analgesic and anti-inflammatory product comprising an acetyl salicylic derivative composition having the formula:

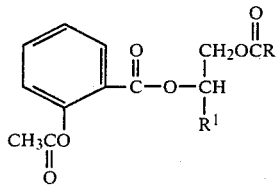

wherein both R and R¹ are hydrocarbon radicals and process for the manufacture thereof.

7 Claims, No Drawings

PHARMACEUTICAL COMPOSITION AND PROCESS FOR THE MANUFACTURE THEREOF

BACKGROUND OF THE INVENTION—FIELD OF THE INVENTION AND DESCRIPTION OF THE PRIOR ART

The present invention relates to new pharmaceutical compounds and to a process for the preparation thereof. In particular, the present invention relates to analgesic and anti-inflammatory compounds.

Acetyl salicylic acid, or aspirin as it is more commonly known, is amongst the most widely used of proprietary medicines. Aspirin can be used in the treatment of numerous ailments and is indicated to have analgesic, anti-inflammatory, antipyretic and antirheumatic activity. However, side effects of the drug may limit its application. For example, acetyl salicylic acid may cause gastric irritation and is contra-indicated where such irritation must necessarily be avoided.

SUMMARY OF THE INVENTION

The object of the present invention is to provide pharmaceutical substances and compositions which exhibit some or all of the advantageous properties of aspirin but in which the contra-indications are minimized.

According to the present invention it has been discovered that certain ester derivatives of acetyl salicylic acid provide useful pharmaceutical activity with minimal contra-indications. The invention provides a pharmaceutical composition containing a glycol ester of acetyl salicylic acid or derivatives thereof. Monoglycol esters have been found suitable.

DETAILED DESCRIPTION OF THE PREFERRED EMBODIMENT

The invention also provides an acetyl salicylic derivative of the formula I:

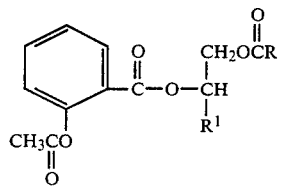

wherein R and $R^1$ which may be the same or different represent any suitable radical such as a hydrocarbon group. The present invention further provides pharmaceutically acceptable derivatives thereof and bioprecursors therefor. Pharmaceutically acceptable derivatives thereof may include acid addition salts.

In a preferred form R may represent an alkyl group. The alkyl group may include for example from 1 to 15 carbon atoms. The alkyl group may be a straight chain alkyl group. In a preferred form R represents a straight chained alkyl group of from 7 to 11 carbon atoms. In a preferred form of the invention $R^1$ represents a lower alkyl group, for example, a methyl, ethyl or propyl group. A methyl group has been found most satisfactory.

Thus by way of example the compounds of the present invention may be of the formula II:

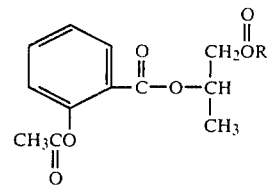

where R is a straight chain alkyl radical having from 1 to 15 carbon atoms and preferably from 7 to 11 carbon atoms.

The compounds of the present invention have analgesic and antiinflammatory activity similar to those of acetyl salicylic acid. It has been found that the following tests provided a valuable guide to the activity of the compounds of the present invention. These tests are the animal model experiments described by L. B. Witkin et al., *J. Pharmacol. Exptl. Therap.*, 133, 400 (1961) and C. A. Winter et al., *Proc Soc, Exp. Biol. Med.*, 111, 544 (1962). The use of compounds of the formula I is particularly advantageous since gastric irritation associated with acetyl salicylic acid therapy is avoided or at least minimized.

The salicylic derivatives of the present invention may be manufactured by any chemical process known to be useful for the manufacture of chemically analagous compounds. A preferred process for the manufacture of a salicylate derivative of the present invention comprises the reaction of an acetyl salicylic acid derivative with a monoglycol ester of the general formula III:

wherein R and $R^1$ have the meanings given above. An acid halide derivative of acetyl salicylic acid, that is an O-acetyl salicyloyl halid such as O-acetyl salicyloyl chloride may be used. The reaction may be undertaken in an inert organic solvent, for example, carbon tetrachloride, chloroform, dichloromethane, acetonitrile, ether, tetrahydrofuran or dioxane or the like.

Compounds of the formula III may be prepared via an acylation reaction of a hydroxyketone of the formula IV.:

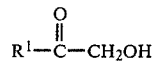

wherein $R^1$ has the meaning given above; with a carboxylic acid of the formula V:

wherein R has the meaning given above; to yield compounds of the formula VI:

A particularly preferred hydroxyketone is the monohydroxy acetone. This yields a monoglycol ester of the formula VII:

VII

This subsequently provides a salicylic acid derivative of the formula II:

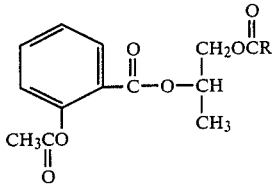

These reactions may be achieved by standard procedures. For example, the acid V may be activated by conversion to an acid halide e.g. the acid chloride prior to coupling with the hydroxyketone. Alternatively the hydroxyketone may be reacted directly with the acid V in the presence of a condensing agent. The condensing agent may be a carbodiimide such as N.N-dicyclohexylcarbodiimide. For a review of these methods reference may be made to J. March, "Advanced Organic Chemistry: Reactions, Mechanisms and Structure", McGraw-Hill, New York, 1968, p. 319–324.

The process is completed by reduction of the intermediates of the formula VI to compounds of formula III. The reduction may be achieved by use of a reducing agent. The reducing agent may be sodium borohydride for example.

Particularly preferred compounds of the present invention exhibiting analgesic and anti-inflammatory activity but with reduced gastric irritation include 2-(Decanolyloxypropyl) O-Acetylsalicylate and 2-(1-Dodecanoyloxypropyl) O-Acetylsalicylate.

A suitable acid-addition salt of a salicylate derivative of the invention is, for example, a salt derived from an organic acid, for example, a hydrochloride, hydrobromide, phosphate or sulphate, or a salt derived from an organic acid, for example an oxalate, lactate, succinate, tartrate, acetate, salicylate, citrate benzoate, B-naphthoate, or adipate.

The salicylate derivatives of the present invention may be administered to animals including man, in the form of a pharmaceutical composition comprising as active ingredient at least one salicylate derivative of the present invention, or an acid-addition salt thereof, in association with a pharmaceutically acceptable diluent or carrier therefor. The composition may further comprise a physiologically acceptable excipient, binder, preservative, stabilizer, flavoring or other compounding ingredient. The composition may be prepared in a conventional unit dosage form as called for by accepted pharmaceutical practice. The composition may be included in soft gelatin capsules, two piece hard gelatin shell capsules, tablets, elixirs, suspensions, emulsions or in injectible solutions or suspensions or oily solutions or suspensions.

The amount of active substances included is selected so as to provide an individual unit dosage, preferably from about 30 milligrams to 1500 milligrams of the active ingredient. Other therapeutically valuable substances may also be included. Caffeine, phenacetin, paracetamol may be used in addition to the active ingredient of the present invention.

The following examples are illustrative of the invention, or of intermediates which may lead to the invention, and represent preferred embodiments but are not to be construed as being limitations thereon. All temperatures are in degrees Celsius.

EXAMPLE 1

1-Decanoyloxypropan-2-one

Monohydroxyacetone was distilled prior to use. Chloroform was distilled from phosphorus pentoxide prior to use. Decanoyl chloride (65 cm$^3$, 0.3146 mole) was added dropwise to stirred solution of monohydroxyacetone (21.8 cm$^3$, 0.3146 mole) and anydrous pyridine (25.4 cm$^3$, 0.3146 mole) in anhydrous chloroform (500 cm$^3$). During the addition the solution was maintained in an ice bath. The mixture was then stirred at room temperature overnight. The solution was washed with water (4×200 cm$^3$) and saturated sodium chloride solution (200 cm$^3$). The organic phase was dried over sodium sulphate and evaporated in vacuo. The resulting oil was distilled to yield 1-decanoyloxypropan-2-one as a mobile liquid, bp 154°–60° (1 mm) (52.4 g, 0.230 mole, 73%),ir (neat) 2860, 1700, 1400, 1340, 1150, 1110 and 1050 cm$^{-1}$; pmr (CDCl$_3$) δ 4.6 (s, 2 H), 2.4 (t, 2 H), 2.1 (s, 3 H), 1.8-1.0 (bm, 14 H) and 0.9 (t, 3 H) ppm.

EXAMPLE 2

1-Decanoyloxypropan-2-one (44.3 g, 0.194 mole) was dissolved in a solution of tetrahydrofuran (1100 cm$^3$) and benzene (200 cm$^3$). After cooling to 5°, ice water (80 cm$^3$) was added. Sodium borohydride (11 g, 0.291 mole) was added to the stirred solution in small proportions to maintain the temperature at 5°. After addition the reaction was stirred at 5° for 45 minutes and glacial acetic acid (14 cm$^3$) was added dropwise. Stirring at 5° was continued for a further 30 minutes. Diethyl ether and chloroform (200 cm$^3$ each) were added and the mixture washed with water (2×200 cm$^3$), a 1% sodium bicarbonate solution (200 cm$^3$) and brine (200 cm$^3$). The organic phase was dried over sodium sulphate and evaporated to yield 1-decanoyloxypropan-2-ol as a colorless liquid (44.0 g, 0.191 mole, 98%), ir (neat) 3600-3100, 2920, 2860, 1730, 1460, 1375, 1240, 1175, 1110, 1055 cm$^{-1}$; pmr (CDCl$_3$) δ 4.0 (m, 2 H), 3.6 (m, 1 H), (D$_2$) m 1 H), 2.3 (t, 2 H), 2.0-1.0 (bm, 17 H) and 0.85 (t, 3 H) ppm.

EXAMPLE 3

2-(1-Decanoyloxypropyl) o-Zcetylsalicylate

A solution of 0-acetylsalicyloyl chloride (12.5 g, 0.0629 mole) in dry carbontetrachloride (25 cm$^3$) was added slowly to a stirred of 1-decanoyloxypropan-2-ol (4.85 g, 0.0211 mole) and dry pyridine (5.1 cm$^3$, 0.0630 mole) in dry carbontetrachloride (150 cm$^3$) at 5°. The solution was then stirred at 25° for two hours and poured over ice (100 g). The mixture was stirred for two hours and the organic layer separated, washed with water, (2×150 cm$^3$), 1% hydrochloric acid, water, 1% sodium bicarbonate, water and brine (2×100 cm$^3$ each), dried over sodium sulphate and evaporated in vacuo. The product was chromatographed on silica gel (500 g) in petroleum ether (40°–60°): ether (80:20) and treated with charcoal in acetone to yield (2(1-decanoyloxypropyl) 0-acetylsalicyate as a colorless liquid (3.4 g. 0.00866 mole, 41%); ir (neat) 2920, 2850, 1770, 1725, 1605, 1480, 1450, 1365, 1290, 1250, 1190, 1160, 1115, 1075, and 915 cm$^{-1}$; pmr (CDCl$_3$) δ 7.9 (dd, 1 H), 7.6-6.9 (m, 3 H), 5.3 (m, 1 H), 4.2 (m, 2, 3 H), 2.3 (m, 2,3 H), 2.3 (m, 2 H) 1,9-1.0 (bm, 17 H) and 0.9 (t, 3 H) ppm.Anal. calcd. for $C_{22}H_{32}O_6$: C, 67.32; H8.22% Found: C, 6725; H, 8.07%.

EXAMPLE 4

1-Dodecanoyloxypropan-2-ol

By replacing decanoyl chloride in Example 1 with dodecanoyl chloride, 1-dodecanoyloxypropan-2-one and subsequently 1-dodecanoyloxypropan-2-ol, as in Example 2, can be obtained.

EXAMPLE 5

2-(1-Dodecanoyloxypropyl) O-Acetylsalicylate

By replacing 1-decanoyloxypropan-2-ol with 1-dodecanoyloxypropan-2-ol in Example 3, 2-(1-dodecanoyloxypropyl) O-acetylsalicylate can be obtained.

Finally, it is to be understood that various other modifications and/or alterations may be made without departing from the spirit of the present invention as outlined herein.

What is claimed is:

1. An analgesic and anti-inflammatory compound having the formula:

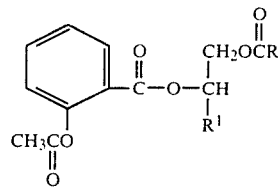

wherein both R and $R^1$ are alkyl radicals.

2. The product of claim 1 wherein R is an alkyl group having 1 to 15 carbon atoms.
3. The product of claim 2 wherein said alkyl group is a straight chain alkyl group.
4. The product of claim 3 wherein said straight chain alkyl group has 7 to 11 carbon atoms.
5. The product of claim 1 wherein $R^1$ is a lower alkyl group.
6. The product of claim 5 wherein $R^1$ is a methyl, ethyl or propyl group.
7. A process for preparing an analgesic anti-inflammatory compound comprising the step of reacting an acetyl salicylic acid derivative with a monoglycol ester having the formula:

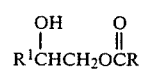

wherein R and $R^1$ are alkyl radicals.

* * * * *